US010488391B2

(12) United States Patent
Hansma et al.

(10) Patent No.: US 10,488,391 B2
(45) Date of Patent: Nov. 26, 2019

(54) NEURAL CIRCUIT PROBE

(71) Applicant: The Regents of the University of California, Oakland, CA (US)

(72) Inventors: Paul K. Hansma, Goleta, CA (US); Kenneth S. Kosik, Santa Barbara, CA (US); Luke S. K. Theogarajan, Carpinteria, CA (US); Barney Drake, Truckee, CA (US); Daniel C. Bridges, Santa Barbara, CA (US); Connor J. Randall, Goleta, CA (US); Kenneth R. Tovar, Portland, OR (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/521,792

(22) PCT Filed: Oct. 30, 2015

(86) PCT No.: PCT/US2015/058409
§ 371 (c)(1),
(2) Date: Apr. 25, 2017

(87) PCT Pub. No.: WO2016/070100
PCT Pub. Date: May 6, 2016

(65) Prior Publication Data
US 2017/0241976 A1    Aug. 24, 2017

Related U.S. Application Data

(60) Provisional application No. 62/073,291, filed on Oct. 31, 2014.

(51) Int. Cl.
*A61N 1/00* (2006.01)
*G01N 33/483* (2006.01)
(Continued)

(52) U.S. Cl.
CPC .......... *G01N 33/4836* (2013.01); *C12M 3/00* (2013.01); *C12M 35/02* (2013.01); *C12M 35/08* (2013.01);
(Continued)

(58) Field of Classification Search
CPC .............. A61N 1/0529; A61B 5/04001; A61B 2562/028; B01J 2219/00371; B82Y 5/00; G01N 33/48728
See application file for complete search history.

(56) References Cited

U.S. PATENT DOCUMENTS 5,445,011 A * 8/1995 Ghislain ................ B82Y 35/00
250/307
6,264,815 B1 * 7/2001 Pethig ..................... B03C 5/005
204/547
(Continued)

FOREIGN PATENT DOCUMENTS

WO    2014160036    10/2014
WO    2015054677    4/2015

OTHER PUBLICATIONS

PCT International Search Report & Written Opinion dated Jan. 29, 2016 for PCT Application No. PCT/US15/58409.
(Continued)

*Primary Examiner* — Mallika D Fairchild
(74) *Attorney, Agent, or Firm* — Gates & Cooper LLP (57) ABSTRACT

A Neural Circuit Probe (NCP) combines a multi-electrode array (MEA) with an automated local probe, wherein the probe is positioned to interact with one or more cells, such as neurons of a neural circuit, grown on or about one or more electrodes of the multi-electrode array. The probe may interact with the cells by electrically recording signals from the multi-electrode array that are assigned to a specific one of the cells. The probe may interact with the cells by locally delivering chemicals to the cells, which transiently and
(Continued)

reversibly modulate the electrical behavior of the cells. The probe may interact with the cells by harvesting the cells using a pipette, so that the harvested cells can be sequenced.

20 Claims, 9 Drawing Sheets

(51) Int. Cl.
    *C12M 3/00*     (2006.01)
    *C12M 1/42*     (2006.01)
    *C12M 1/36*     (2006.01)
    *G01N 15/10*     (2006.01)

(52) U.S. Cl.
    CPC ..... *C12M 41/48* (2013.01); *G01N 2015/1006* (2013.01)

(56) References Cited

U.S. PATENT DOCUMENTS

| | | | |
|---|---|---|---|
| 2009/0012446 A1 | 1/2009 | Cui et al. | |
| 2011/0125050 A1* | 5/2011 | Bau | B01L 3/0275 600/547 |
| 2012/0225435 A1 | 9/2012 | Seger et al. | |
| 2013/0231290 A1* | 9/2013 | Wu | A61K 31/13 514/17.8 |
| 2014/0380531 A1* | 12/2014 | Ukraintsev | G01Q 10/065 850/3 |

OTHER PUBLICATIONS

Kang et al., "Nanofountain Probe Electroporation of Single Cells" Nano Lett., vol. 13, No. 6 (2013) [online] [retrieved on Jan. 4, 2016]. Retrieved from the Internet <URL: http://www.ncbi.nlm.nih.gov/pmc/articles/PMC3736975/> p. 1, 2, 4, 8.
Li et al., "High resolution imaging using scanning ion conductance microscopy with improved distance feedback control" Progress in Natural Science, vol. 18, p. 671-677 (2008) [online] [retrieved on Jan. 4, 2016]. Retrieved from the Internet <URL: https://www.researchgate.net publication/243333766_High_resolution_imaging_using_scanning _ion_conductance_microscopy_with_improved_distance_feedback_control> entire document, especially p. 672, 675, 676.
Potter et al., "Closing the Loop: Stimulation Feedback Systems for Embodied MEA Cultures" 2005 [online] [retrieved on Jan. 4, 2016]. Retrieved from the Internet <URL: https://neurolab.gatech.edu/wp/wp-content/uploads/potter/publications/Potter4MEAbookCOLpub.pdf> entire document, especially p. 1-4.
Kosik, K.S., "Study neuron networks to tackle Alzheimer's", Nature, Nov. 7, 2013, pp. 31-32, vol. 503.
Chong, S.A., et al., "Synaptic dysfunction in hippocampus of transgenic mouse models of Alzheimer's disease: A multi-electrode array study", Neurobiology of Disease, 2011, pp. 284-291, vol. 44.
Dossi, E., et al., "Multi-electrode Array Recordings of Human Epileptic Postoperative Cortical Tissue", Journal of Visualized Experiments, Oct. 2014, pp. 1-9, vol. 92, e51870.
Hansma, P.K., et al., "The Scanning Ion-Conductance Microscope", Science, Feb. 3, 1989, pp. 641-643, vol. 243.
Takami, T., et al., "Nanopipette exploring nanoworld", Nano Convergence, 2014, pp. 1-12, vol. 1., No. 17.
Nadappuram, B.P., et al., "Fabrication and Characterization of Dual Function Nanoscale pH-Scanning Ion Conductance Microscopy (SICM) Probes for High Resolution pH Mapping", Analytical Chemistry, 2013, pp. 8070-8074, vol. 85.
Morris, C.A., et al., "Local pH Measurement with Scanning Ion Conductance Microscopy", Journal of the Electrochemical Society, 2013, pp. H430-H435, vol. 160, No. 8.
Zhou, L., et al., "Measuring Ions with Scanning Ion Conductance Microscopy", The Electrochemical Society Interface, 2014, pp. 47-52.
Actis, P., et al., "Electrochemical Nanoprobes for Single-Cell Analysis", ACS Nano, 2014, pp. 875-884, vol. 8, No. 1.
Rheinlaender, J., et al., "Mapping the Mechanical Stiffness of Live Cells With the Scanning Ion Conductance Microscope", Soft Matter World Newsletter, Jun. 2013, pp. 1-3, vol. 53.
Schaffer, T.E., "Nanomechanics of Molecules and Living Cells with Scanning Ion Conductance Microscopy", Analytical Chemistry, 2013, pp. 6988-6994, vol. 85.
Miragoli, M., et al., "Side-specific mechanical properties of valve endothelial cells", Am. J. Physiol Heart Circ Physiol, 2014, pp. H15-H24, vol. 307.
Babakinejad, B., et al., "Local Delivery of Molecules from a Nanopipette for Quantitative Receptor Mapping on Live Cells", Analytical Chemistry, 2013, pp. 9333-9342, vol. 85.
Iwata, F., et al., "Local electroporation of a single cell using a scanning ion conductance microscope", Japanese Journal of Applied Physics, 2014, pp. 1-5, 036701, vol. 53.
Liu, B-C., et al., "Scanning ion conductance microscopy: a nanotechnology for biological studies in live cells", Frontiers in Physiology, Jan. 2013, pp. 1-6, vol. 3, Article 483.
Lab, M.J., et al., "The scanning ion conductance microscope for cellular physiology", Am. J. Physiol Heart Circ Physiol, 2013, pp. H1-H11, vol. 304.
Fei, Z., et al., "Optical Nanoscopy and Novel Microscopy Techniques: Scanning ion conductance microscopy", (CRC Press, 2014).
Kornyei, Z., et al., "Cell sorting in a Petri dish controlled by computer vision", Scientific Reports, 2013, pp. 1-10, vol. 3., No. 1088.
Yang, R., et al., "Development of Automated Patch Clamp System for Electrophysiology", IEEE Conference on Robotics and Biomimetics (ROBIO), 2013, pp. 2185-2190.
Yang, R., et al., "Analysis of Visual-based Micromanipulation for Patch Clamp Recording", IEEE Conference on Robotics and Biomimetics, 2014, pp. 487-492.
Buzsaki, G., et al., "Tools for Probing Local Circuits: High-Density Silicon Probes Combined with Optogenetics", Neuron, Apr. 8, 2015, pp. 92-105, vol. 86.
Claverol-Tinture, E., et al., "Extracellular potentials in low-density dissociated neuronal cultures", Journal of Neuroscience Methods, 2002, pp. 13-21, vol. 117.
Richiardi, J., et al., "Correlated gene expression supports synchronous activity in brain networks", Science, Jun. 12, 2015, pp. 1241-1244, vol. 348, No. 6240.
Steinmeyer, J.D., et al., "High-Throughput Single-Cell Manipulation in Brain Tissue", PLoS ONE, Apr. 2012, pp. 1-10, vol. 7, No. 4.
Kodandaramaiah, S.B., et al., "Automated whole-cell patch clamp electrophysiology of neurons in vivo", Nat Methods, Jun. 2012, pp. 585-587, vol. 9, No. 6.
Magdesian, M.H., et al., "Atomic Force Microscopy Reveals Important Differences in Axonal Resistance to Injury", Biophysical Journal, Aug. 2012, pp. 405-414, vol. 103.
Shenai, M.B., et al., "A Novel MEA/AFM Platform for Measurement of Real-Time, Nanometric Morphological Alterations of Electrically Stimulated Neuroblastoma Cells", IEEE Transactions on Nanobioscience, Jun. 2004, pp. 111-117, vol. 3, No. 2.
Liao, Y., et al., "The Subread aligner: fast, accurate and scalable read mapping by seed-and-vote", Nucleic Acids Research, 2013, pp. 1-17, e108, vol. 41, No. 10.

* cited by examiner

NEURAL CIRCUIT PROBE

CROSS REFERENCE TO RELATED APPLICATIONS

This application claims the benefit under 35 U.S.C. Section 119(e) of the following and commonly-assigned application:

U.S. Provisional Application Ser. No. 62/073,291, filed on Oct. 31, 2014, by Paul K. Hansma, Kenneth S. Kosik, Luke Theogarajan, Barney Drake, Daniel C. Bridges, Connor Randall, and Kenneth Tovar, entitled "NEURAL CIRCUIT PROBE,"; which application is incorporated by reference herein.

STATEMENT REGARDING FEDERALLY SPONSORED RESEARCH AND DEVELOPMENT

This invention was made with Government support under Grant No. R01-GM065354 awarded by the National Institutes for Health (NIH). The Government has certain rights in this invention.

BACKGROUND OF THE INVENTION

1. Field of the Invention

The invention is related to scanning probe microscopy, and more specifically, a neural circuit probe based on probes used in scanning ion conductance microscopy and multi-electrode arrays.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

Recently, it has been argued that studying neuron networks at the mesoscopic scale may be a path to understanding Alzheimer's disease and other neurodegenerative diseases where the interaction of neurons is believed to be key to the pathophysiology [1]. Multi-electrode arrays (MEAs) are powerful tools for monitoring the electrical behavior of small collections of neurons in mesoscopic neuron networks. MEAs made it possible to highlight synaptic dysfunction in the hippocampus of a transgenic mouse models of Alzheimer's disease in young animals well before the typical amyloid or tau pathology was evident [2]. MEAs were also used to measure the spatio-temporal patterns of spontaneous interictal and evoked seizure-like events and the mechanisms underlying seizure onset and propagation in human epileptic postoperative cortical tissue [3]. A new company, Neuroproof, is using MEAs for phenotypic drug screening.

One limitation of MEAs is that there has been no way to unambiguously identify the contribution of a specific neuron to the network behavior or to analyze the biochemistry of neurons that are found to play a special role in the network.

One way to identify specific cells such as individual neurons is through scanning probe microscopy. Scanning probe microscopy is a family of related techniques for providing images of surfaces and for providing information about the mechanical, electrical and magnetic properties of surfaces. For example, atomic force microscopy (AFM) provides for very high-resolution scanning of surfaces, on the order of nanometers. Another example is scanning ion conductance microscopy (SICM), which provides high resolution images of soft surfaces such as cell surfaces without contacting the surfaces.

Recently, new SICM [4] probes have been developed that extend its capabilities to include local measurements of specific ion concentrations [5], pH [6,7], electrical potential gradients [8], oxygen consumption [9], cell mechanical properties [10-12], the delivery of molecules for quantitative receptor mapping [13] and electroporation [14]. These new probes and techniques, reported in just the past two years, have been used on a variety of cell types including neurons. Earlier work on cells, beginning with the pioneering work of Korchev and his group, and including work on protein localization on the surface of cells, is well summarized in recent reviews [15-17].

Thus, there is a need in the art for combining these technologies. The present invention satisfies this need.

SUMMARY OF THE INVENTION

To overcome the limitations in the prior art described above, and to overcome other limitations that will become apparent upon reading and understanding this specification, this invention discloses a method and apparatus for investigating cells, comprising a neural circuit probe (NCP) that combines a multi-electrode array (MEA) with an automated local probe, wherein the automated local probe is positioned to the interact with one or more cells grown on or about one or more electrodes of the multi-electrode array.

A controller implements a feedback system for an automated approach of the probe to the multi-electrode array, wherein the controller uses proportional and integral feedback or threshold detection to position the probe based on one or more input signals from the probe, such as ion current or electrical resistance. The probe is positioned in X and Y directions to center it in a field of view of a microscope. The multi-electrode array is translated in X and Y directions to bring the cells under the probe. The probe is then automatically lowered in a Z direction by the controller to above the cells. The probe may be positioned to within half an inner diameter of the probe's tip, e.g., to within a distance of about 0.5-10 µm.

In one embodiment, the cells being investigated comprise a neural circuit, wherein the neural circuit is comprised of one or more neurons.

The probe may interact with the cells by electrically recording signals from the cells. For example, the probe may perform mobile electrical recording that assigns the electrically recorded signals to a specific one of the cells.

The probe may interact with the cells by locally delivering chemicals to a specific one of the cells. For example, the locally delivered chemicals may transiently and reversibly modulate the electrical behavior of the specific one of the cells.

The probe may interact with the cells by harvesting a specific one of the cells. For example, the probe may comprise a pipette used to harvest the specific one of the cells.

BRIEF DESCRIPTION OF THE DRAWINGS

Referring now to the drawings in which like reference numbers represent corresponding parts throughout.

DETAILED DESCRIPTION OF THE INVENTION

In the following description of the preferred embodiment, reference is made to a specific embodiment in which the invention may be practiced. It is to be understood that other embodiments may be utilized and structural changes may be made without departing from the scope of the present invention.

Overview

This invention comprises a Neural Circuit Probe (NCP) that combines a SICM-inspired automated local probe with a MEA, wherein the probe is positioned to the interact with one or more cells, such as neurons of a neural circuit, grown on or about one or more electrodes of the MEA.

The probe is called "SICM-inspired," because it uses the same basic mechanism for sensing the surface as in SICM [4], but the probes used would not actually be useful for SICM, because the opening is too large to give good images. The NCP is not in any sense a SICM, in that the NCP does not use the probe to image a surface and is thus not a scanning probe microscope of any kind.

These two technologies are combined for mobile electrical recording, local chemical delivery, and single cell harvesting from a neural circuit comprised of neurons grown on the MEA using the probe. Specifically, the probe may interact with the cells by electrically recording signals that are assigned to a specific one of the cells. In addition, the probe may interact with the cells by locally delivering chemicals to a specific one of the cells, which transiently and reversibly modulate the electrical behavior of the specific one of the cells. The probe may also interact with the cells by harvesting a specific one of the cells using a pipette. These and other aspects of this invention are disclosed in more detail below.

Technical Disclosure

Description of the NCP

Figure 1:
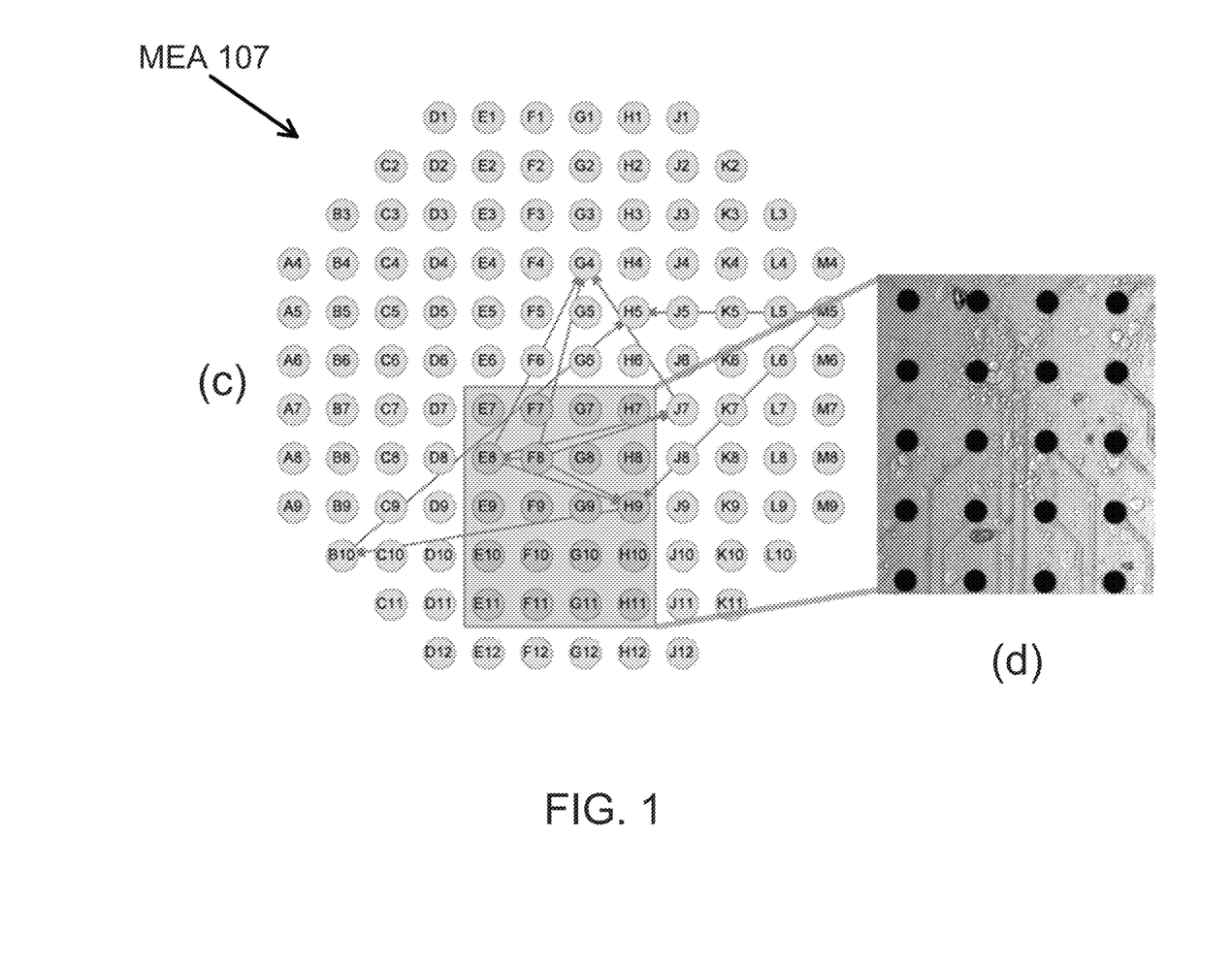
FIGS. 1(a)-1(d) illustrate a neural circuit probe according to an embodiment of the present invention.
Figure 1A:
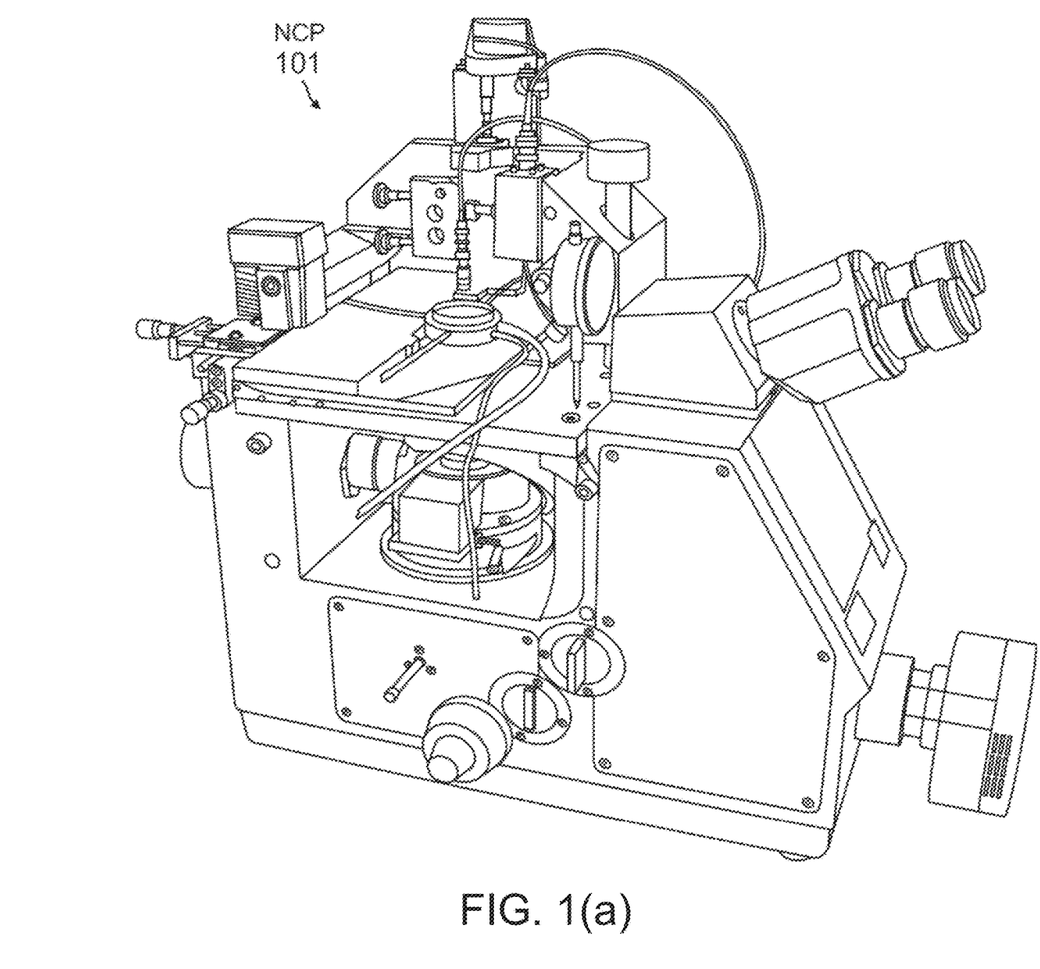

FIG. 1(a) is an image of a prototype NCP 101 situated on an inverted microscope, according to one embodiment of the present invention.

Figure 1B:
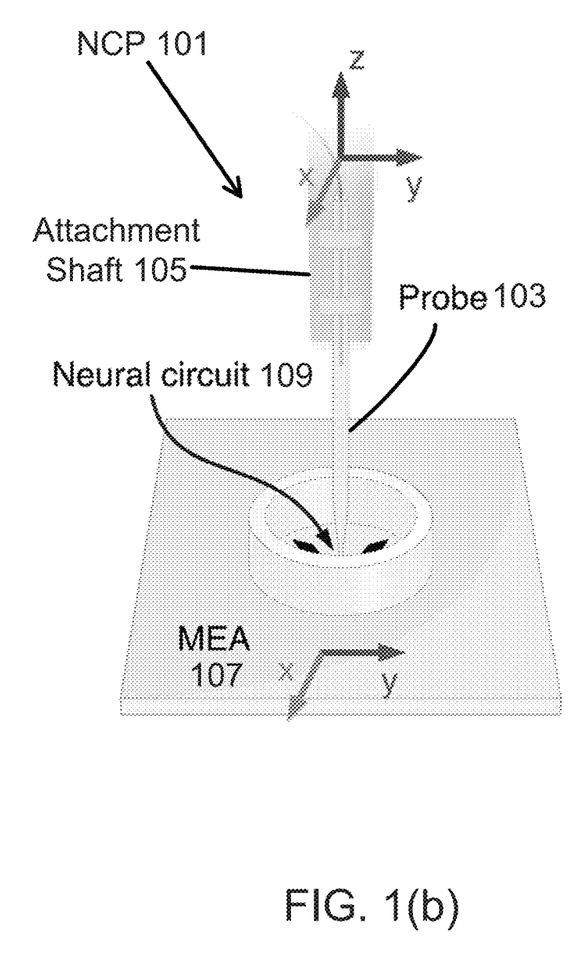

FIG. 1(b) is a schematic drawing providing a general description of the NCP 101, which includes a replaceable, automated, local probe 103 mounted on an attachment shaft 105 and positioned over a MEA 107, upon which is grown a neural circuit 109 comprised of one or more neurons. Preferably, the attachment shaft 105 and probe 103 can be positioned in X-Y-Z directions and the MEA 107 can be positioned in X-Y directions, as indicated by the arrows.

FIG. 1(c) is a top-view schematic drawing of the MEA 107, which includes electrodes labeled as A4-A9, B3-B10, C2-C11, D1-D12, E1-E12, F1-F12, G1-G12, H1-H12, J1-J12, K2-K11, L3-L10 and M4-M9. Causal relations are shown as arrows between the electrodes, resulting in a functional connectivity graph. FIG. 1(d) is an image of a portion of the MEA 107, comprising electrodes E7-E11, F7-F11, G7-G11 and H7-H11.

Other components of the instrument may include a controller (not shown) with an operator interface that implements a simple feedback system for automated approach of the probe 103 to the MEA 107.

Preferably, the probe 103 is positioned in X and Y directions to center it in the field of view of the microscope. Then, the MEA 107 is translated in X and Y directions to bring a target neuron or other cell of the neural circuit 109 directly under the probe 103. Finally, the probe 103 is automatically lowered in the Z direction, with controller feedback, to just above, but not touching, the target neuron.

Preferably, the controller uses proportional and integral feedback or threshold detection control to position the probe 103, and can accept a variety of input signals, such as ion current or electrical resistance used in the SICM-inspired probes. For example, with threshold detection, the controller would monitor the ion current into the pipette and automatically lower the probe 103 in the Z direction until it decreased below a threshold (typically 0.25 to 5% below the value of ion current measured far above the sample). When the threshold is reached, the lowering is stopped leaving the pipette typically a fraction of its inner diameter above the surface.

An amplifier may be located on the NCP 101 head unit that amplifies the current signal before being transmitted to the controller.

The operator interface for the controller allows the operator to engage and disengage the probe 103 using feedback, and may also be used to control the location of the MEA 107 beneath the probe 103, allowing the operator to position the probe 103 above neurons of interest in the MEA 107.

Figure 5:
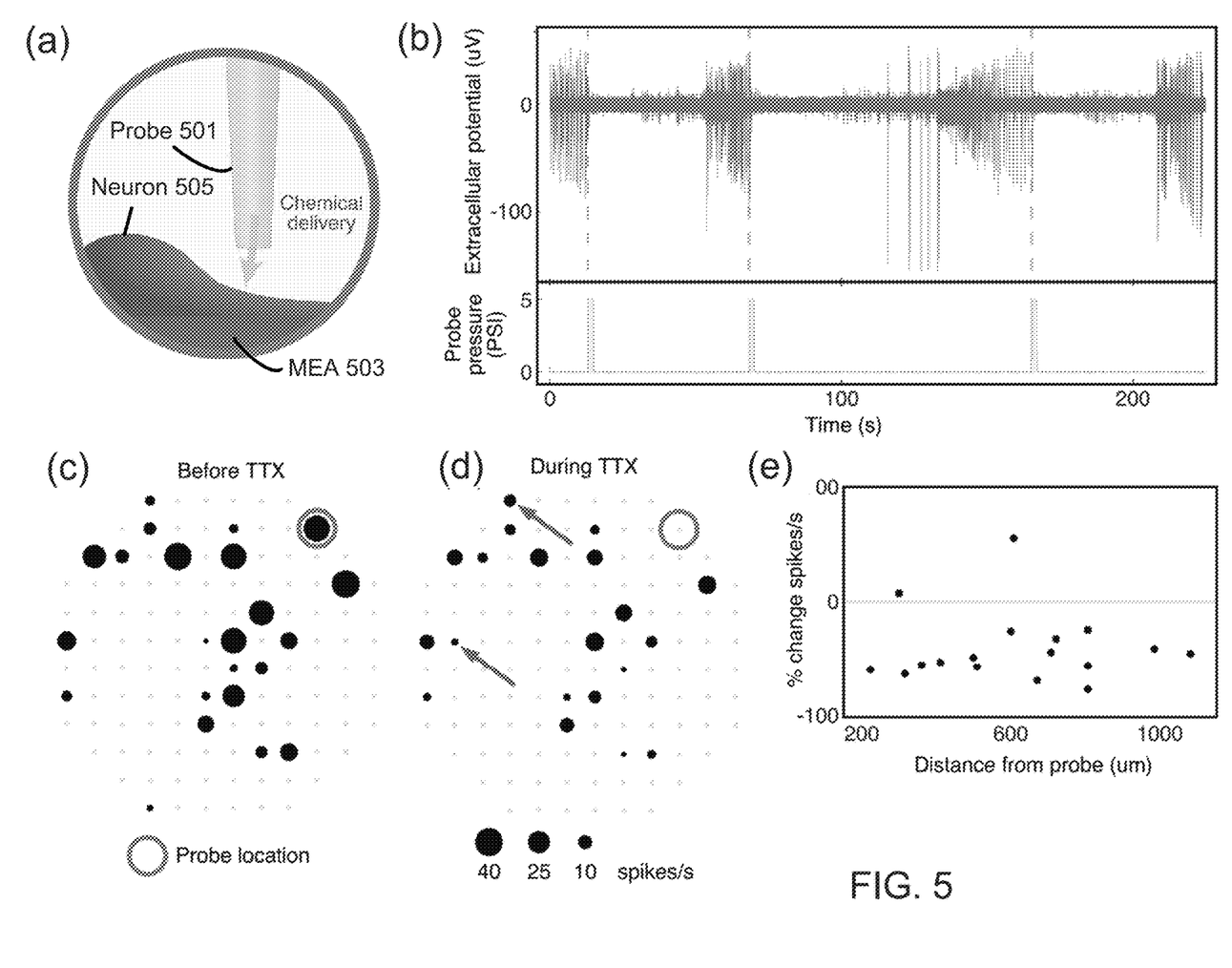
FIGS. 5(a)-5(e) illustrate transient targeted neuronal silencing using the neural circuit probe.
Figure 6:
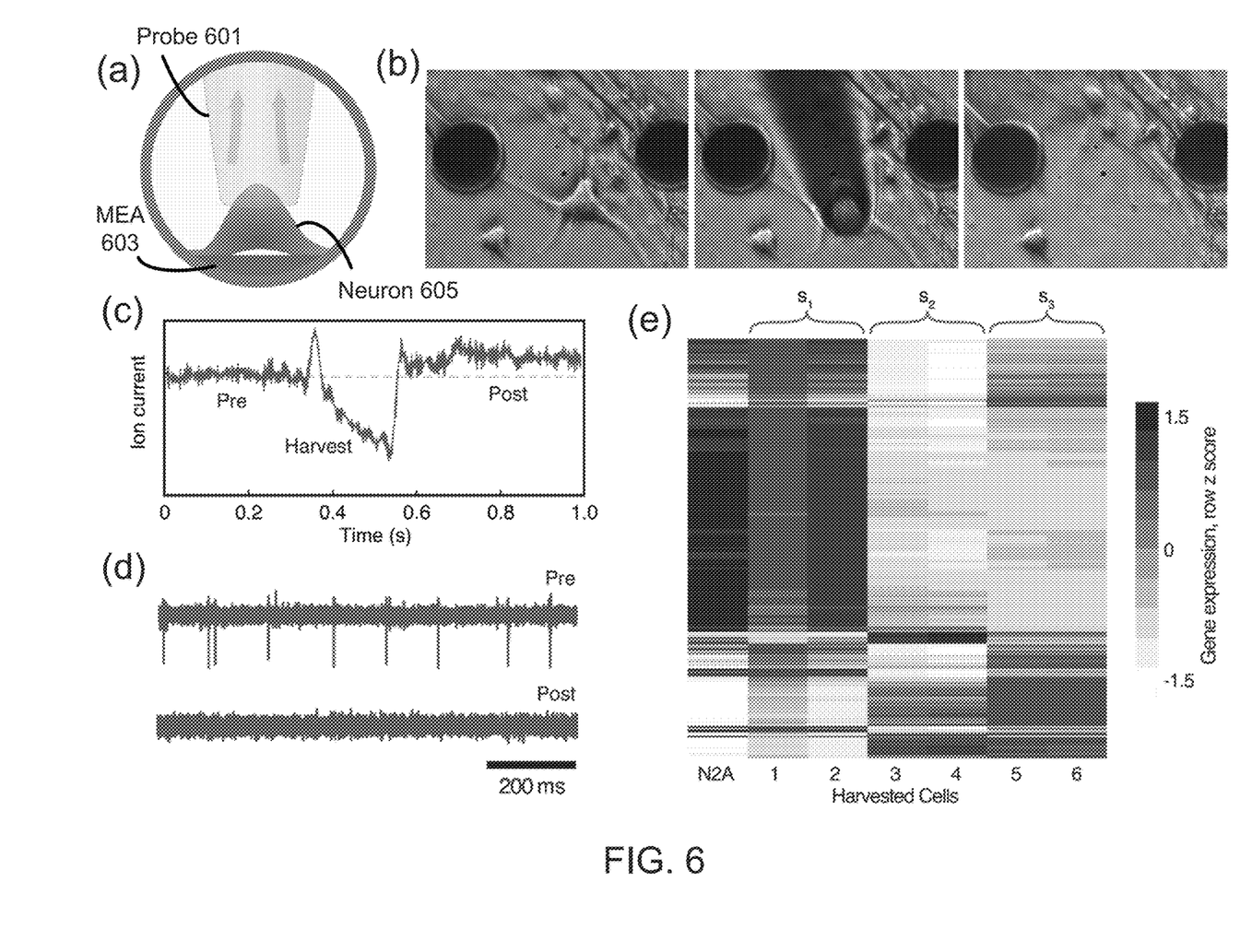
FIGS. 6(a)-6(e) illustrate how the neural circuit probe is used to harvest cells of interest from the multi-electrode array.

A pneumatic control system (not shown) may be attached to the probe 103 to regulate a pressure line for chemical delivery (as shown in FIG. 5) and a vacuum line for cell harvesting (as shown in FIG. 6). These are discussed in more detail below. Moreover, an integrated pressure sensor (not shown) may be connected to the MEA 107 to measure the duration and magnitude of pressure or vacuum application for temporal alignment with the MEA 107 signal.

Components of the NCP

Figure 2:
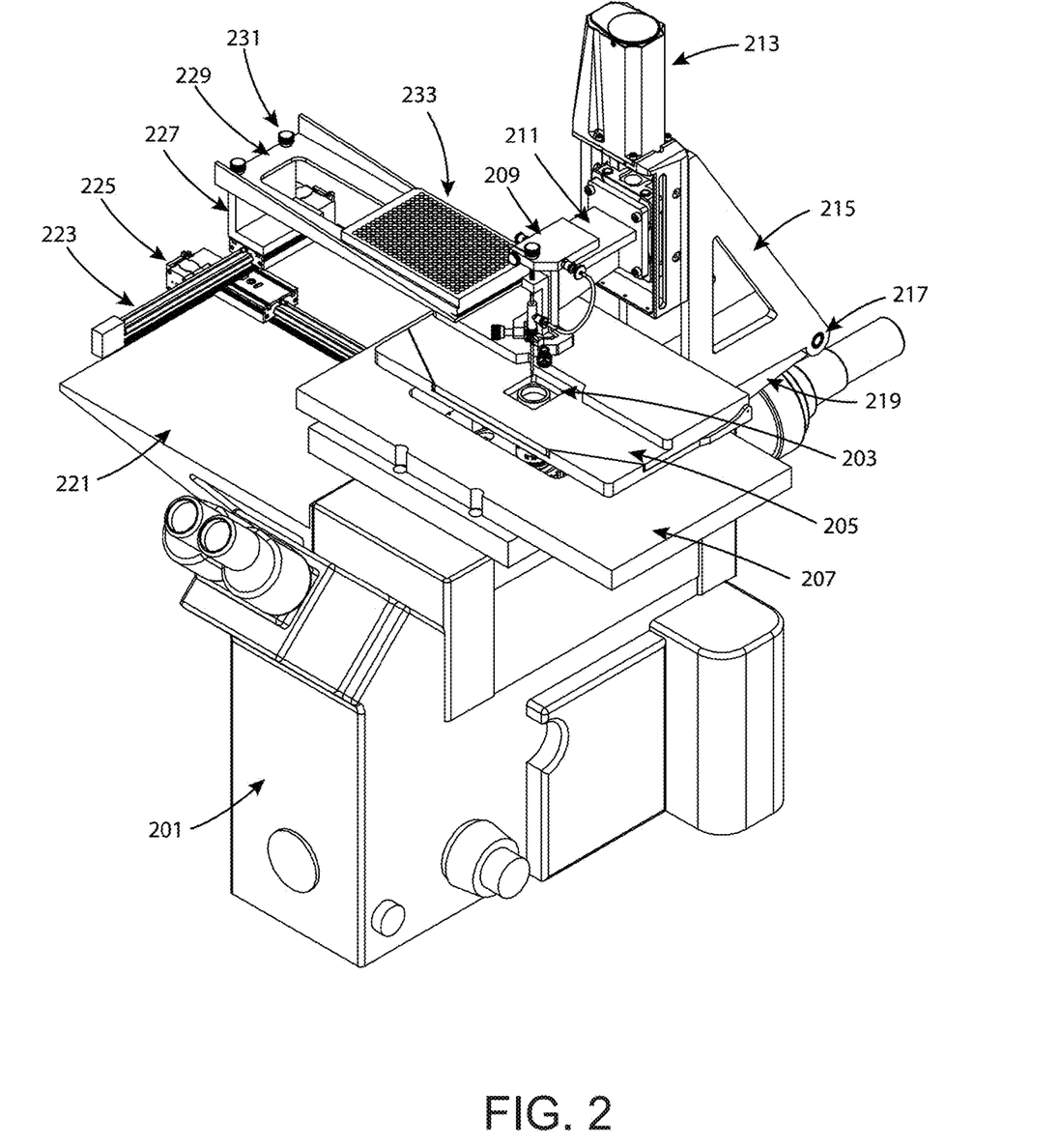
FIG. 2 is a schematic drawing of the specific components of the NCP, according to one embodiment of the present invention.

FIG. 2 is a schematic drawing of the specific components of the NCP, according to one embodiment of the present invention. The NCP includes an inverted microscope 201, and a MEA 203 connected to a MEA amplifier 205 and secured to a precision X Y translation stage 207. A head stage 209 is secured to a kinematic head stage mount 211, which is fixed to a precision Z translation stage 213. The Z translation stage 213 is secured to the inverted microscope 201 through a Z translation stage bracket 215 that rotates around a bearing 217 fitted to a base mount 219, which attaches to pre-existing mounting holes on the inverted microscope 201.

A translation stage mounting plate 221 is fixed to pre-existing mounting holes on the left side of the inverted microscope 201. A Y translation stage 223 is mounted perpendicular to a X translation stage 225. A multiwell base bracket 227 supports a multiwell bracket 229 and is secured with two multiwell thumbscrews 231, allowing for the multiwell bracket 229 to be removed when not in use. A multiwell plate 233 locks to the multiwell bracket 229 for cell harvesting.

The entire NCP shown in FIG. 2 can optionally be placed in a Faraday cage for electromagnetic shielding and/or a sterile bench to help maintain sterility of the neurons.

Figure 3:
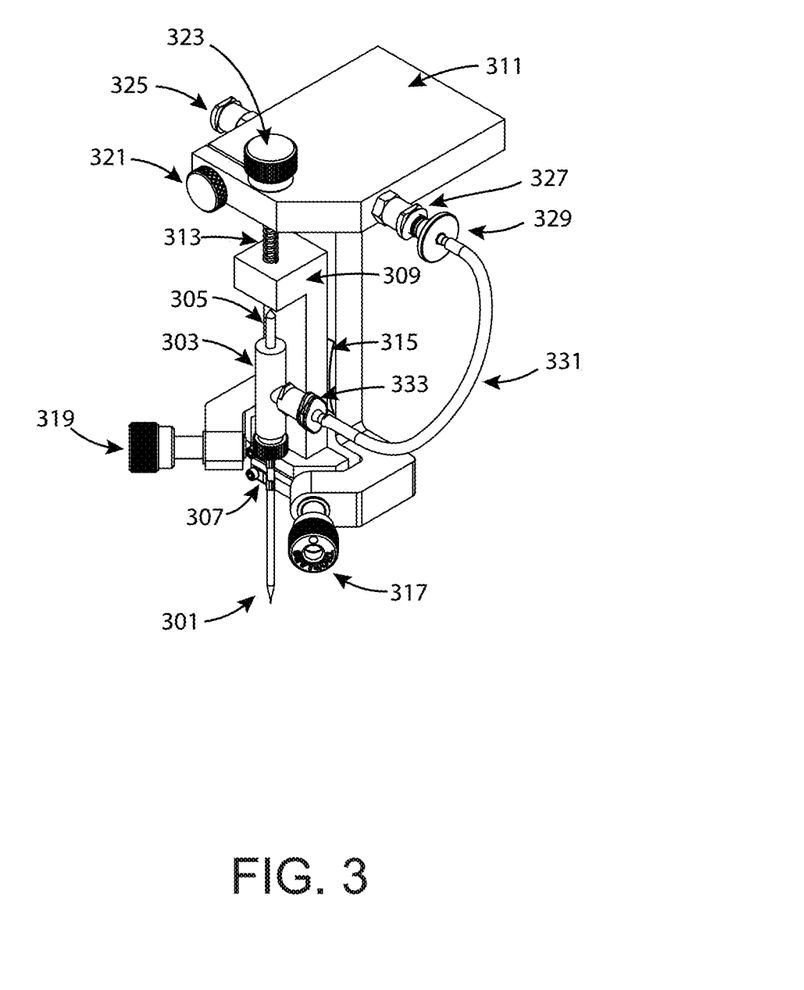
FIG. 3 is a schematic drawing of a head stage of the head unit, according to one embodiment of the present invention.

FIG. 3 is a more detailed view of the head stage 209, according to one embodiment of the present invention. A pipette 301 is attached to a pipette holder 303 by a spring clip 307 and a v-groove in a pipette translator 309. The pipette holder 303 has an electrode pin 305 that will connect to an external controller for feedback during the approach. The pipette translator 309 is connected to a pipette translator base 311 through a flexure 313 that consists of a rod to provide lateral stiffness, and a compression spring, to provide a normal force acting in the direction along the long axis of the rod. This normal force pushes on both the pipette translator 309 and a pipette translator base 311, and is used to aid in the Z translation adjustment. A Z translation locking thumbscrew 321 secures a flexure 313. A Z translation adjustment 323 contains internal threads matching the thread pattern on the end of the flexure 313 that allows for Z translation of the entire pipette translator relative to the pipette translator base 311. Two lateral adjustments can be made through lateral adjustment knobs 317 and 319. Pressure can be applied to the pipette 301 in order to dispense chemicals locally to cells in the MEA 203. Additionally, a vacuum can be applied to the pipette 301 in order to harvest cells from the MEA 203 to be dispensed in the multiwell plate 233. Luer fittings 325 and 327 are connected to the pipette translator base 311 as a strain relief with a through hole to transmit pressure or vacuum through luer adapters 329 and 333, pressure line 331, pipette holder 303, and finally to the pipette 301.

The head stage 209 can also be placed in an initial adjustment stand on which it is indexed with the same kinematic mount (a ball in a grove, in a slot and on a flat) as onto 211. This initial adjustment stand has two video microscopes, one horizontal and one vertical looking up, focused at the tip of the pipette 301. These microscopes allow visualization of positioning of the tip of the pipette vertically with adjustment knob 323 and horizontally with the lateral adjustment knobs 317 and 319. Thus, the position of the pipette can be adjusted before the head stage 309 is put onto the apparatus shown in FIG. 2.

In the preferred embodiment, there are multiple head stages 309 (for example, 3) ready to be put onto the apparatus shown in FIG. 2. In this way, different pipettes, such as a smaller, 2 micron diameter one for delivering chemicals to the cells, and a larger, 20 micron diameter one for electrical recording or cell harvesting, and a spare 20 micron diameter one if the first gets clogged, can be ready to be quickly interchanged. The adjustment stand may be equipped with ultraviolet sterilization in order to sterilize the pipette 301 to prevent infecting cells in the MEA 203.

Probe position and movement is controlled by a microcontroller interfaced to a host computer. Cells of interest for probing or harvesting will be selected by the operator or by computer programs that analyze the neural circuit data collected by the MEA 203 and MEA amplifier 205 to determine cells of interest. The operator can choose cells on the computer through a live video view of the sample as seen through a microscope with optional phase contrast or by using fluorescent tagging. The user interface displays overlaid meta-data onto the video display, such as electrode identification tags, over rapid navigation. The current implementation of the software is written in C and Swift.

The operator will be able to initiate an automated sequence in which the XY stage 207 translates the sample under study to put a selected cell directly under the pipette 301 and then the precision Z translation stage 313 lowers the pipette while monitoring the ion current into the pipette. When, in threshold detection mode, the ion current decreases a preset amount (of order 0.25 to 5%), the pipette lowering is automatically stopped with the pipette positioned a distance of order the inner diameter of the pipette above the sample, as in Scanning Ion Conductance Microscopy [4]. Alternately, once an operator engages the instrument, the controller will automatically position and lower the probe under proportional-integral feedback by sampling the pipette electrical resistance. This resistance is increased as the probe closely approaches the surface. Automatic detection of surface approach can position the probe to within 0.5-10 µm, depending upon pipette inner diameter. Once located at the surface, the probe will perform its desired action.

Signals are Assigned to Specific Cells

FIGS. 4(a)-4(f) illustrate the monitoring of electrical activity of a selected neuron using a probe incorporating a mobile electrode. Specifically, the NCP was switched from a SICM approach mode to an electrical recording mode.

Figure 4:
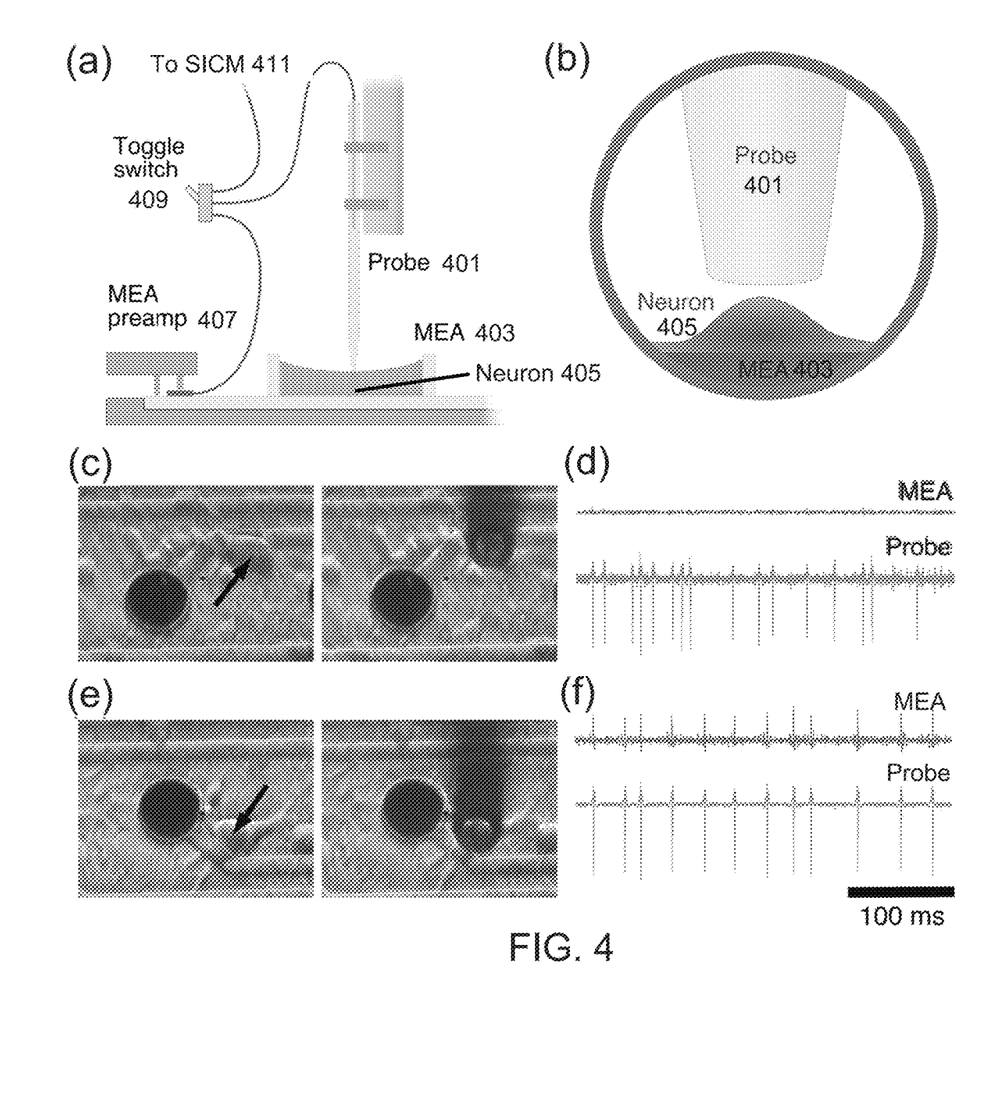
FIGS. 4(a)-4(f) illustrate the monitoring of electrical activity of a selected neuron using the neural circuit probe.

FIG. 4(a) shows a probe 401, MEA 403 and neuron 405, wherein the probe 401 incorporates a mobile electrode to measure extracellular potentials anywhere on the MEA 403, thereby providing a higher spatial resolution of the signal as compared to a standard MEA. In one embodiment, the probe 401 is comprised of a 20 micron inner diameter pipette with a 75 micron platinum electrode inserted in the top [22]. One of 120 channels of a MEA pre-amplifier 407 is repurposed to measure and record signals from the mobile electrode of the probe 401. A toggle switch 409 connects the mobile electrode of the probe 401 with a SICM controller 411 for approaching the surface of a neuron.

The repurposed channel can be tapped into using a small piece of conductive film with an insulating layer on the backside, bypassing the electrode on the MEA 403, and inserting the mobile signal. This technique was necessary to validate the actual neuron that gave rise to the MEA 403 signal of interest. For example, this permitted precise identification of the active neuron of interest for cell harvesting.

As shown in FIG. 4(b), the SICM-inspired approach mode allows the probe 401 to be automatically positioned to within a fraction of the inner diameter of the probe 401 above any neuron 405 in the neural circuit on the MEA 403.

FIGS. 4(c) and 4(d) indicate that no spiking activity was detected on the MEA 403 for the neuron closest to the MEA 403 electrode. FIG. 2(c) comprises a pair of images, wherein the arrow in the first image identifies the neuron and the black circle comprises the MEA 403 electrode, and the second image shows the MEA 403 electrode (the black circle) with the probe 401 positioned above the neuron. FIG. 2(d) is a graph of MEA 403 and probe 401 signals on a 100 ms scale, wherein the simultaneous recording from the mobile electrode of the probe 401 shows robust spiking behavior as compared to the MEA 403.

FIGS. 4(e) and 4(f) indicate that the MEA 403 electrode closest to the neuron showed spiking, but when the mobile electrode of the probe 401 was positioned directly over the cell, the corresponding recording had a higher signal-to-noise ratio. FIG. 4(e) comprises a pair of images, wherein the arrow in the first image identifies the neuron and the black circle comprises the MEA 403 electrode, and the second image shows the MEA 403 electrode (the black circle) with the probe 401 positioned above the neuron. FIG. 4(f) is a graph of MEA 403 and probe 401 signals on a 100 ms scale, wherein the simultaneous recording from the mobile electrode of the probe 401 shows spiking behavior for both the MEA 403 and probe 401.

Specific Cells are Targeted for Local Chemical Delivery

In addition to monitoring the signals from specific neurons, FIGS. 5(*a*)-5(*e*) illustrate transient targeted neuronal silencing, wherein targeted local chemical delivery with the NCP can be used to modify their electrical behavior. This was done with probes comprised of smaller pipettes, typically with inner diameters of 1-2 microns.

In one experiment, application of the Na+ channel blocker tetrodotoxin (TTX, 500 nM) caused a temporary and reversible cessation of activity from that cell. Charged molecules could be delivered with the use of a multi-barreled pipette, where one barrel is used for SICM-inspired approach, and the others for chemical delivery. Thus, the NCP can do targeted drug delivery with high spatial resolution.

FIG. 5(*a*) shows a probe 501, MEA 503 and neuron 505, wherein the drug delivery probe 501 is positioned over the neuron 505 on the MEA 503, and the probe 501 is automatically lowered with SICM feedback to a fraction of its inner diameter (typically less than a micron for this application).

FIG. 5(*b*) are graphs of time (s) vs. probe pressure (PSI) and time vs. extracellular potential (uV) that shows that a transient increase of probe 501 pressure delivered TTX (500 nM), which reversibly blocked spiking activity, with high spatial resolution. This process was repeated 3 times.

FIGS. 5(*c*) and 5(*d*) illustrate the firing rates at all electrodes of the MEA 503 before TTX application (in FIG. 5(*c*)) and during TTX application (in FIG. 5(*d*)), wherein the black dots are sized according to the number of spikes per second (and electrodes with no active spiking are shown as gray dots). When spiking was blocked at a specific electrode (embedded within a circle to indicate probe 501 location), it had widespread effects on the firing rates observed at other MEA 503 electrodes, as shown before TTX application (in FIG. 5(*c*)) and during TTX application (in FIG. 5(*d*)). Although the firing rate decreased for many electrodes (as indicated by comparing the size of the black dots in FIG. 5(*c*) and FIG. 5(*d*)), for two electrodes it increased (as indicated by the arrows in FIG. 5(*d*)).

FIG. 5(*e*) is a graph of distance from the probe 12 (μm) vs. % change in spikes per seconds, which shows that the decrease in firing rate was independent of the distance of the probe 501 from the drug delivery site, indicating that TTX delivery was localized. Thus, changes in the firing rate at other electrodes are consistent with a network effect resulting from blocking spiking activity at the target electrode, not due to diffusion of TTX.

Specific Cells Are Harvested

FIGS. 6(*a*)-6(*e*) illustrate how the NCP can be used to harvest cells of interest from the MEA, wherein these harvested cells can then be analyzed by various techniques. Specifically, FIGS. 6(*a*)-6(*e*) illustrate harvesting a selected neuron for single cell RNA sequencing (RNA-seq).

FIG. 6(*a*) shows a probe 601, MEA 603 and neuron 605, wherein the neuron 605 was selected based on the extracellular recordings measured with the MEA 603, and then the controller was used to position the probe 601 above the neuron 605. During an automated approach, the ion current is used as feedback to lower the probe 601 over the cell 605. Once the vertical position of the probe 601 is fixed, the piezo is held at a constant voltage, a vacuum is applied to the probe 601 and suction is used to harvest a cell 605, wherein the cell 605 is removed from the network and temporarily stored in the pipette of the probe tip 601.

Confirmation of cell pickup is obtained visually as well as by monitoring the SICM current, as shown in FIGS. 6(*b*) and 6(*c*), respectively.

FIG. 6(*b*) is a sequence of optical three images before, during and after cell harvesting. From left to right in the sequence, a first image shows two black circles comprising the MEA 603 electrodes with a neuron 605 therebetween, a second image shows the two black circles comprising the MEA 603 electrodes with the probe 601 positioned directly above the neuron 605, and a third image shows the two black circles comprising the MEA 603 electrodes with the neuron 605 removed.

FIG. 6(*c*) is a graph of time (s) vs. ion conductance current, which is used as verification of cell harvesting. Three distinct regions are visible in the ion conductance current signal during cell harvesting:
- (Pre) after fixing the vertical position of the probe 601, but before harvesting,
- (Harvest) as the cell 605 is harvested from the surface of the MEA 603, it plugs the pipette of the probe 601 causing a drop in the ion current, and
- (Post) the ion current stabilizes at a slightly higher level because the distance to the surface after cell 605 pick up is greater than the distance to the top of the cell 605 before cell 605 pick up.

It can be seen that a drop in the current occurs (from pre-harvest), as the neuron 605 is harvested, due to the cell 605 transiently increasing the resistance at the micro pipette probe tip 601 (during harvest). Once the neuron 605 is inside the pipette, but past the tip 601, the current increases again, slightly higher than the initial current because the cell body is no longer just below the tip 601, allowing more current to pass (post-harvest).

FIG. 6(*d*) is a graph of MEA 603 signals on a 200 ms scale, which shows that spiking is no longer detected at a MEA 603 electrode near the neuron 605 after the cell 605 is harvested (upper trace for Pre vs. lower trace for Post).

After confirmation of cell harvesting, the cell 605 is deposited into a polymerase chain reaction (PCR) tube by applying pressure to the pipette and the cell 605 is then processed for RNA-seq. FIG. 6(*e*) is a heatmap analysis of the RNA-seq results of 6 different neurons harvested using the NCP as compared to a single Neuro2A cell used as a control, wherein cell types (S1, S2 and S3), not accessible otherwise and defined by their transcriptome are highlighted. Analyses of this type can dovetail with a recent study showing that resting-state functional networks correlate with the orchestrated activity of dozens of genes linked to ion channel activity and synaptic function [23].

Advantages And Improvements

Although the NCP currently uses probes from Scanning Probe Microscopy, it is not a Scanning Probe Microscope. It does not use the probes for generating images. The imaging is with optical microscopy, which is much faster. The probes are used for monitoring, modification and harvesting of individual neurons. There may also be benefits to combining the imaging of Scanning Probe Microscopes with MEAs, but the resulting instrument would not be called an NCP. For example, an Atomic Force Microscope (AFM) was combined with a custom-built MEA to measure, for the first time, electrically induced morphological changes in neurons [27].

Though it is difficult to anticipate all future applications for the NCP, it already seems clear that it will join the armamentarium being used to understand the complex relationship between functional and anatomical connectivity of neurons as well as the equally complex relationship between physiological function and the transcriptional profile. Low hanging fruit will be testing of neural circuit models by reversibly knocking out critical neurons, determining the re-organized functional connectivity map and comparing these results to network models.

In the context of the present research, the NCP was used for non-contact local electrical recording. It is also possible to incorporate recent developments in pipette-based automated patch clamps [19,25]. Three simple changes would be needed to adapt their groundbreaking technology for use in the NCP: (1) a vertical rather than angled approach, (2) lateral translation of the probe only to center it in the field of the optical microscope, and (3) high precision automatic lateral translation of the sample to position the cell of interest under the probe.

This disclosure has focused on the use of pipette probes. There are, however, other probes from other Scanning Probe Microscopes that may be useful, as described in more detail below. For example, an NCP with cantilever-based force probes from AFM, inspired by the work of Magdesian et al., who used AFM to reversibly compress individual axons [26]. It turned out that pipette probes acting on somas were much easier to implement than force probes acting on neurites. The optical imaging of somas vs.

neurites was easier, especially in the crowded cultures that are more active. Further, the neurites tended to slip out from under the force probe, but these are not insurmountable difficulties.

Other technology exists for single cell harvesting that use machine vision to identify cells and to locate a pipette near the cell for harvesting [18]. The vertical positioning accuracy of the pipette is limited to the depth of field of the objective, limiting how close the pipette can approach a cell (often ~10 microns). For localized drug delivery and cell harvesting it is ideal to have the pipette approach the cell as close as possible in order to minimize disrupting nearby cells. The present invention uses current feedback for vertical positioning, allowing the pipette to approach well within half the inner diameter of the pipette tip, up to a user defined threshold. This enables very local drug delivery, monitoring cell activity with an electrode within the pipette, and cell harvesting.

Technology exists that enables for an automated approach with a pipette to come into contact with cells [19,20]. The device has a pipette that approaches cells from an angle and is used as an automated patch clamp system for electrophysiology on cells in a petri dish. The device approaches to within 20-30 microns above a substrate where the position of the pipette tip and the cell can be located. The motor will center the pipette over the cell and then a feedback loop is used to approach the cell at 100 nm increments while monitoring the pipette resistance until there is a change indicating the pipette has come into contact in order to make a seal with the cell membrane. Once the pipette is in contact and has made a seal with the cell membrane then the instrument can obtain electrophysiological recordings. The present invention is a multi-purpose instrument used on a MEA that is capable of cell harvesting, drug delivery, and obtaining extracellular recordings with a mobile electrode that does not require contact with the cell membrane.

The local delivery of TTX clearly shows the potential for delivering other chemicals for a number of purposes. This includes high-throughput, efficient, reliable, and combinatorial delivery of various genetic vectors and reagents into targeted cells with techniques that could be implemented into future NCPs [24]. The combination of: (1) the automated, indexed lateral translations stage together with (2) the novel, automated vertical approach of the pipette to just above the surface of neurons, and (3) an automated pressure cycle for chemical delivery will make it possible to just touch a screen with an optical image of the neurons to select one or more locations for chemical delivery and then touch a button to initiate a completely automated chemical delivery protocol. There is no fundamental reason why the complete sequence could not completed in a few seconds, thus opening the door to more complex modifications involving multiple neurons sequentially.

Local modification of a monitored neural network will be useful in discriminating between network models. A strong test of a network model will be to see if it correctly responds to the removal, electrically, of a specific neuron. If a neuron is found to have an important role in a network in this way, then the NCP can isolate and monitor the electrical behavior of that neuron and, with the same pipette, pick it up for biochemical analysis such as the single cell RNA-seq described here.

Many other probes exist that are useful for probing neurons, such as high density silicon probes and tetrode probes [21], but these have not, to our knowledge, been combined with MEAs.

Experimental Setup

The following further describes the experimental setup used with one embodiment of this invention.

Multi-electrode array recordings:

Multi-electrode array recordings were taken using a MultiChannel

Systems MEA2100 amplifier. Recordings were sampled at 20 kHz using 120 count electrode MEAs with electrode diameter of 30 µm and inter-electrode spacing of 100 µm.

Instrumentation:

MEA stage x-y motion is provided by two computer controlled stepper motors (Thorlabs model Z812B). Probe x-y position is manually adjusted, gross z motion is provided by a computer controlled stepper motor (SAIA model UBD2N), and fine z motion is provided by a piezo stack with 18 µm range.

Controller:

Custom control firmware was developed in C for an ARM Cortex M4 microcontroller, interfaced to a standard laptop computer. The piezo control voltage was generated using proportional integral control updated at 18 kHz. Custom user interface software was developed in Python to allow for point and click positioning of the MEA stage and interaction with the control system. Source code is available upon request.

Cell cultures:

Primary cultures were prepared from C57BL/6 mice. Briefly, hippocampi were dissected from postnatal day 1 mice, dissociated using papain and trituration, then plated on a monolayer of glia at a density of 250-500 cells/mm2. Cells were incubated at 37° C. with 5% $CO_2$ and maintained in MEM supplemented with 5% heat inactivated fetal calf serum and Mito+ serum extender. Media changes occurred every 3-4 days. All measurements were taken between 7 and 21 days in vitro. All animal usage was performed following University of California, Santa Barbara Institutional Animal Care and Use Committee (IACUC) approved protocols.

Neuro2A cells were obtained from ATCC and cultured in EMEM containing 10% FBS at 37° C. with 5% CO2.

Single-cell RNA-seq:

Neuro2A cells were harvested using trypsin and washed once with PBS. After counting, the cells were diluted to a concentration of 1 cell per ul. 1 ul of this 92 cell suspension was used for RNA-seq as described below.

Before harvest of primary culture, media was replaced with PBS. Single cells harvested by the NCP were ejected in a ~1 μl drop into a 200 μl PCR tube containing 9.5 μl of water with RNAse inhibitors. Cells were lysed, cDNA generated and preamplified using the SMART-seq v4 kit from Clontech according to manufacturer's directions. Libraries were built using 250 pg of preamplified cDNA using the Nextera XT DNA sample preparation kit. Barcoded libraries were pooled and sequenced on a Nextseq 500 using 75 reads cycles.

Raw reads were aligned to the mouse genome using Bowtie 228 and summarized using the Rsubread library [28]. Genes for which at least 10 reads were obtained in at least 2 of the samples were kept (6631 genes) and all other genes were discarded from the analysis. The resulting data was denoised using singular value decomposition. A hierarchical clustering based on the euclidian distance of both the genes and samples was used to order the expression matrix before the row-normalized, color coded resulting expression was plotted as a heat map.

Alternative Probe Configurations

Figure 7:
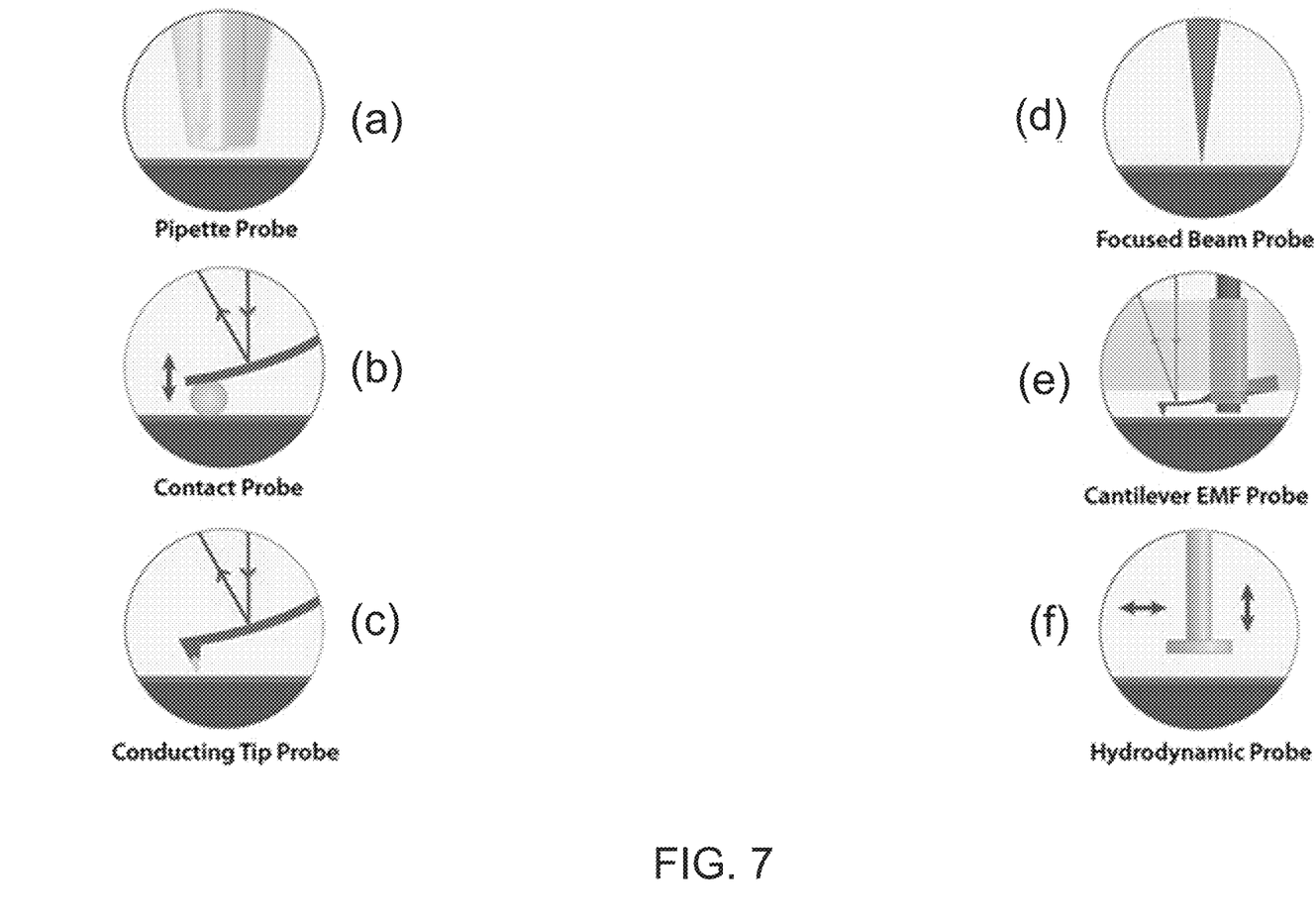
FIGS. 7(a)-7(f) illustrate interchangeable probe tips that may be used with the neural circuit probe.

The circular callouts in FIG. 7 labeled as 7(a)-7(f) illustrate interchangeable probes that may be used with the NCP to investigate novel ways to stimulate and sense neural circuits, wherein FIG. 7(a) is a multi-barreled micro-pipette probe that can be used to deliver chemicals locally as well as record electrochemical signals, FIG. 7(b) is a contact probe comprised of a micro-bead attached to a conventional AFM cantilever in order to apply a precise force to specific locations in the neural network, FIG. 7(c) is a conducting tip probe used to measure local electrical signals, as well as electrically stimulate neural networks, with controlled force to prevent damage to the neurons, FIG. 7(d) is a focused visible or IR beam probe for stimulation through light and heat, FIG. 7(e) is a cantilever-guided magnetic stimulation or sensing probe, and FIG. 7(f) is a hydrodynamic probe comprised of a cylindrical piston that is actuated with a piezo in the vertical and horizontal direction to provide a hydrodynamic force. Each of these interchangeable probe tips are described in more detail in the parent provisional application cross-referenced above and in the discussion below.

With regard to FIG. 7(a), the multi-barreled micro-pipette probe is positioned above the neural cell bodies, axons or axonal bundles, dendritic branches or even single synapses using an ion conductance signal from one of the barrels. The other barrels allow for local chemical delivery or physical stimulation by fluid flow. The other barrels can also be used as pH or chemical sensors. Another embodiment would be to use one barrel for SICM, one or more barrels for delivery of chemicals, and one or more barrels to withdraw the delivered chemicals with the purpose of localizing the effect of the chemicals. This localization could even be sub cellular since pipette openings smaller than 100 nm are commonly used for SICM, while neuron cell bodies are typically many microns in width. The localization of the chemicals could be constrained even more if the tip of the delivery pipette were surrounded by a larger diameter pipette to remove the delivered chemical. Finally, note that it may be possible to use the same pipette barrel to do a SICM-inspired approach as well as electrical recording of neuron activity since the SICM-inspired control current is slowly varying, on the time scale of seconds or minutes depending on NCP stability, while the spikes of neuron activity are fast signals on the time scale of milliseconds or below. Thus, one electrode in the SICM-inspired barrel could monitor the slowly varying background to control pipette position and the spikes of neural activity. In an alternate embodiment, the one electrode could be gated between the two activities of controlling position and monitoring spikes.

With regard to FIG. 7(b), the contact probe can be used to apply a wide range of forces and pressures to the neural network depending on the stiffness and tip geometry used. Preliminary research conducted with this probe has already found an effect on action potentials, specifically rapid action potential firing during disruption. Also, this probe has been used to precisely sever specific neuronal connections. This type of stimulation could become more sensitive, as well as reversible, with a softer probe. This probe can also search for small displacements of the surface of axons that result from the changing electrostatic forces as charges rearrange during action potentials.

With regard to FIG. 7(c), the conducting tip probe can be used to study the force dependence of the electrical signals (how things change when the buffer that naturally comes between an electrode surface and a neuron is squeezed out by force), as well as to sense membrane potentials by intracellular probing of neurons at higher forces with sharp probes as a less destructive patch-clamp-like platform capable of inferring micro-circuitry. This will provide precise local measurements that are more difficult to pinpoint with a MEA alone because the electrodes on the MEA are in fixed positions that may or may not coincide with a cell or axon of interest. Thus, there is a huge advantage in being able to have a mobile electrode, based on conducting tip AFM or pipettes as in FIG. 7(a), to position directly over a cell body, axon, synapse or other feature of interest. The conducting tip probe can also be used to electrically stimulate the neurons at specific locations. Local stimulation with the probe tip could simulate transcranial Direct Current Stimulation (tDCS). This could be tested locally with the conducting tip probe by using the small conductive tip as an electrode and also place a larger electrode in the MEA solution or on the cantilever base. The current density would be high near the tip to either stimulate or inhibit activity depending on the polarity of the applied potential.

With regard to FIG. 7(d), the focused beam probe, such as an infrared laser light beam, has been shown to excite or suppress neural activity. There is a large field of optogenetics, which uses genetically modified cells to provide a pathway for using light to control neurons. This could also be implemented in the NCP either with a focused beam or an optical fiber. The optical fiber could be combined with a SICM-inspired pipette in a geometry as shown in FIG. 7(a) for the pipette to provide positioning information. Alternatively, the light could be guided down one or more barrels of a pipette to control the neurons.

With regard to FIG. 7(e), the generalized cantilever Electro-Magnetic Field (EMF) probe is also proposed to stimulate and detect magnetic fields. This probe can also be used in conjunction with the micro-pipette probe to locally deliver chemicals. Additionally, the EMF probe can be used to stimulate the neural network, similar to Transcranial Magnetic Stimulation (TMS).

With regard to FIG. 7(f), the hydrodynamic probe provides a hydrodynamic force to the target to simulate the traumatic fluid flows in the brain associated with impacts to the head. The probe is comprised of a cylindrical head that is attached to a piezo to rapidly translate the cylinder along the vertical axis for pressure waves or the horizontal axis for shear waves.

It is noted that the above description of FIGS. 7(a)-7(f) is not intended to be exhaustive, and other types of probes may be used with the NCP of this invention. Specifically, the NCP can serve as a rapid prototyping system for possible sensing and actuation methods. Also, another type of probe could consist of a multi-electrode sensor, positioned over a region of interest, to record local field potentials at a higher spatial resolution than the multi-electrode array below the cells to be monitored. This mobile multi-electrode sensor could have an array of electrodes at a spacing significantly smaller than those typically used on the array below the sample, and could either be held stationary or scanned over the cells. The mobile multi-electrode sensor could incorporate a pipette for surface detection or could use an alternate method.

REFERENCES

The following publications are incorporated by reference herein:
1. Kosik K. S., Diseases: Study neuron networks to tackle Alzheimer's. Nature. 503, 31 (2013).
2. Chong S. A. et al., Synaptic dysfunction in hippocampus of transgenic mouse models of Alzheimer's disease: a multi-electrode array study. Neurobiol. Dis. 44, 284-291 (2011).
3. Dossi E., Blauwblomme T., Nabbout R., Huberfeld G., Rouach N., Multi-electrode Array Recordings of Human Epileptic Postoperative Cortical Tissue. J. Vis. Exp., 1-9 (2014).
4. Hansma P. K., Drake B., Marti O., Gould S. A., Prater C. B., The scanning ion-conductance microscope. Science. 243, 641-643 (1989).
5. Takami T., Park B., Kawai T., Nanopipette exploring nanoworld. Nano Converg. 1, 17 (2014).
6. Nadappuram B. P., McKelvey K., Al Botros R., Colburn A. W., Unwin P. R., Fabrication and characterization of dual function nanoscale pH-scanning ion conductance microscopy (SICM) probes for high resolution pH mapping. Anal. Chem. 85, 8070-8074 (2013).
7. Morris C., Chen C.-C., Ito T., Baker L., Local pH Measurement with Scanning Ion Conductance Microscopy. J. Electrochem. Soc. 160, H430-H435 (2013).
8. Zhou L., Zhou Y., Baker L. A., Measuring Ions with Scanning Ion Conductance Microscopy. ECS Interface, 47-52 (2014).
9. Actis P. et al., Electrochemical nanoprobes for single-cell analysis. ACS Nano. 8, 875-884 (2014).
10. Rheinlaender J., Schäffer T. E., Mapping the mechanical stiffness of live cells with the scanning ion conductance microscope. Soft Matter. 9, 3230 (2013).
11. Schäffer T. E., Nanomechanics of molecules and living cells with scanning ion conductance microscopy. Anal. Chem. 85, 6988-6994 (2013).
12. Miragoli M. et al., Side-specific mechanical properties of valve endothelial cells. AJP Hear. Circ. Physiol. 307, H15-H24 (2014).
13. Babakinejad B. et al., Local Delivery of Molecules from a Nanopipette for Quantitative Receptor Mapping on Live Cells. Anal. Chem. 85, 9333-9342 (2013).
14. Iwata F., Yamazaki K., Ishikazi K., Ushiki T., Local electroporation of a single cell using a scanning ion conductance microscope. Jpn. J. Appl. Phys. 53 (2014).
15. Liu B. C. et al., Scanning ion conductance microscopy: a nanotechnology for biological studies in live cells. Front. Physiol. (2013).
16. Lab M. J., Bhargava A., Wright P. T., Gorelik J., The scanning ion conductance microscope for cellular physiology. AJP Hear. Circ. Physiol. (2012).
17. Fei Z., Shi H., Zhang Y., Gu Y., Scanning ion conductance microscopy. Optical Nanoscopy and Novel Microscopy Techniques, P. Xi, Ed. (CRC Press, 2014).
18. Környei, Z., Beke, S., Mihálffy, T., Jelitai, M., Kovács, K. J., Szabó, Z., & Szabó, B. (2013). Cell sorting in a Petri dish controlled by computer vision. Scientific reports, 3.
19. Yang R., Lai W. C. K., Xi N., Yang J., Development of automated patch clamp system for electrophysiology. 2013 IEEE Int. Conf. Robot. Biomimetics, 2185-2190 (2013).
20. Yang, R., Tam, C. H., Cheung, K. L., Wong, K. C., & Lai, K. W. Analysis of Visual-based Micromanipulation for Patch Clamp Recording.
21. Buzsáki, György, Eran Stark, Antal Berényi, Dion Khodagholy, Daryl R. Kipke, Euisik Yoon, and Kensall D. Wise. "Tools for Probing Local Circuits: High-Density Silicon Probes Combined with Optogenetics." Neuron 86, no. 1 (2015): 92-105.
22. Claverol-Tinture E., Pine J., Extracellular potentials in low-density dissociated neuronal cultures. J. Neurosci. Meth. 117, 13-21 (2002).
23. Richiardi J., et al., Correlated gene expression supports synchronous activity in brain networks. Science. 348, 1241-1244 (2015).
24. Steinmeyer J. D., Yanik M. F., High-throughput single-cell manipulation in brain tissue. PLoS One. 7 (2012).
25. Kodandaramaiah S. B., Franzesi G. T., Chow B. Y., Boyden E. S., Forest C. R., Automated whole-cell patch clamp electrophysiology of neurons in vivo. Nat. Methods. 9, 585-587 (2012).
26. Magdesian M. H. et al., Atomic force microscopy reveals important differences in axonal resistance to injury. Biophys. J. 103, 405-414 (2012).
27. Shenai M. B. et al., A novel MEA/AFM platform for measurement of real-time, nanometric morphological alterations of electrically stimulated neuroblastoma cells. IEEE Trans. Nanobioscience. 3, 111-117 (2004).
28. Liao Y., Smyth G. K., Shi W., The Subread aligner: fast, accurate and scalable read mapping by seed-and-vote. Nucleic Acids Res. 41, e108 (2013).

Conclusion

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:
1. An apparatus for investigating cells, comprising:
a neural circuit probe (NCP) comprised of a multi-electrode array (MEA) comprising a plurality of electrodes, an automated local probe, and a controller, wherein the multi-electrode array records signals from one or more cells grown on or about one or more electrodes of the plurality of electrodes of the multi-electrode array, the probe incorporates a mobile electrode that records signals from the one or more cells grown on or about the one or more electrodes of the plurality of electrodes of the multi-electrode array, and the controller positions both the multi-electrode array and the automated local probe based on the signals recorded from the mobile electrode of the probe and the signals recorded from the one or more electrodes of the plurality of electrodes of the multi-electrode array, so that both the multi-electrode array and the automated local probe interact with the one or more cells grown on or about the one or more electrodes of the plurality of electrodes of the multi-electrode array.

2. The apparatus of claim 1, wherein the controller implements a feedback system for an automated approach of the automated local probe to the multi-electrode array.

3. The apparatus of claim 2, wherein the neural circuit probe further comprises a microscope, and the automated local probe is positioned in X and Y directions to center it in a field of view of the microscope.

4. The apparatus of claim 3, wherein the multi-electrode array is translated in X and Y directions to bring the cells under the automated local probe.

5. The apparatus of claim 4, wherein the automated local probe is automatically lowered in a Z direction by the controller to a position above the cells.

6. The apparatus of claim 3, wherein the cells are selected by an operator using the microscope.

7. The apparatus of claim 2, wherein the controller uses proportional and integral feedback or threshold detection to position the automated local probe based on one or more input signals.

8. The apparatus of claim 7, wherein the input signals comprise an ion current or electrical resistance input from the automated local probe.

9. The apparatus of claim 7, wherein the automated local probe is positioned to a vertical position within half an inner diameter of the automated local probe's tip.

10. The apparatus of claim 9, wherein the automated local probe is positioned to within a distance of 0.5-10 µm.

11. The apparatus of claim 1, wherein the cells comprise a neural circuit.

12. The apparatus of claim 11, wherein the neural circuit is comprised of one or more neurons.

13. The apparatus of claim 1, wherein the automated local probe interacts with the cells by electrically recording signals from the cells.

14. The apparatus of claim 13, wherein the automated local probe performs mobile electrical recording that assigns the electrically recorded signals to a specific one of the cells.

15. The apparatus of claim 1, wherein the automated local probe interacts with the cells by locally delivering chemicals to a specific one of the cells.

16. The apparatus of claim 15, wherein the locally delivered chemicals transiently and reversibly modulate the electrical behavior of the specific one of the cells.

17. The apparatus of claim 1, wherein the automated local probe interacts with the cells by harvesting a specific one of the cells.

18. The apparatus of claim 17, wherein the automated local probe comprises a pipette used to harvest the specific one of the cells.

19. The apparatus of claim 1, wherein the cells are selected by analyzing data collected by the multi-electrode array.

20. A method of investigating cells, comprising:
operating a neural circuit probe (NCP) comprised of a multi-electrode array (MEA) comprising a plurality of electrodes, an automated local probe, and a controller, wherein the multi-electrode array records signals from one or more cells grown on or about one or more electrodes of the plurality of electrodes of the multi-electrode array, the probe incorporates a mobile electrode that records signals from the one or more cells grown on or about the one or more electrodes of the plurality of electrodes of the multi-electrode array, and the controller positions both the multi-electrode array and the automated local probe based on the signals recorded from the mobile electrode of the probe and the signals recorded from the one or more electrodes of the plurality of electrodes of the multi-electrode array, so that both the multi-electrode array and the automated local probe interact with the one or more cells grown on or about one or more electrodes of the plurality of electrodes of the multi-electrode array.

* * * * *